US007319895B2

United States Patent
Klefstad-Sillonville et al.

(10) Patent No.: US 7,319,895 B2
(45) Date of Patent: Jan. 15, 2008

(54) GARMENT FOR THE MEDICAL MONITORING OF A PATIENT

(75) Inventors: Francis Klefstad-Sillonville, Bouc Bel Air (FR); Jean-Luc Weber, Salon de Provence (FR); David Blanc, Montfort sur Argens (FR)

(73) Assignee: Tam-Telesante (FR)

( * ) Notice: Subject to any disclaimer, the term of this patent is extended or adjusted under 35 U.S.C. 154(b) by 370 days.

(21) Appl. No.: 10/916,143

(22) Filed: Aug. 11, 2004

(65) Prior Publication Data

US 2005/0034485 A1    Feb. 17, 2005

(30) Foreign Application Priority Data

Aug. 14, 2003    (FR)    ................................. 03 09937

(51) Int. Cl.
*A61B 5/04*    (2006.01)
(52) U.S. Cl. ........................ 600/388; 600/389; 600/390
(58) Field of Classification Search ......... 600/388–390
See application file for complete search history.

(56) References Cited

U.S. PATENT DOCUMENTS

| 6,381,482 | B1 | 4/2002 | Rajamanickam et al. | |
|---|---|---|---|---|
| 6,687,523 | B1* | 2/2004 | Jayaramen et al. | ......... 600/388 |
| 2001/0000526 | A1 | 4/2001 | Gopinathan et al. | |
| 2002/0124295 | A1 | 9/2002 | Hatch et al. | |

FOREIGN PATENT DOCUMENTS

WO    WO 01/02052 A    1/2001

* cited by examiner

*Primary Examiner*—Lee S. Cohen
(74) *Attorney, Agent, or Firm*—Alston & Bird LLP

(57) ABSTRACT

A flexible, elastic garment (1) is provided comprising biomedical sensors (3, 4, 5, 6), an electrical power distribution and data transmission bus (2, 7) and a coupling circuit for allowing contactless transmission of power and data between the sensors and a circuit external to the garment. The sensors (3, 4, 5, 6), and the bus (2, 7) for distributing the electrical power and/or transporting the data from the sensors in the garment are formed by elastic conducting yarns integrated into the fabric of the garment.

11 Claims, 3 Drawing Sheets

GARMENT FOR THE MEDICAL MONITORING OF A PATIENT

FIELD AND BACKGROUND OF THE INVENTION

The present invention relates to a garment for the medical monitoring of a subject.

The medical monitoring of persons undergoing their usual activities or in their usual situations is useful in many cases, where the monitoring means must not disrupt or disturb the subject's life, for example during clinical trials for novel therapeutic means or methods and also in the case of the elderly, the state of health of whom it is desired to monitor, remotely, in their natural way of life in order to maintain their autonomy as long as possible.

In other applications, both medical surveillance and medical assistance have to be almost permanent when the patient is exposed to a dangerous situation that may occur randomly in his activity or his situation and may require prompt assistance. Such cases occur, for example, with individuals in a high-risk situation (fire fighters, military personnel on missions, maintenance personnel in high-risk installations, top sportsmen, etc.) or with newborns at risk of sudden infant death, or young children suffering from cardio-respiratory disorders.

Quasi-continuous medical monitoring requires the lasting attachment on to the patient, of biomedical sensors relating to the disorder or the risk being monitored. For example, cardio-respiratory functions are very frequently monitored by means of electrocardiograms (ECG) and respiratory measurements. The corresponding sensors may be an impediment to the patient if they are bulky or heavy, or difficult to take out on oneself during the medical monitoring phases, and their power supply means (generally batteries) may be heavy or bulky. Solutions have been proposed to reduce the impediment due to the sensors, to the batteries or cells, and to the data processing modules that are associated therewith and attached to the patient by fastening the sensors and the modules to a garment that the patient slips on and wears throughout his monitored activities (WO-A-99/64657).

These known solutions have the drawback of generally using electrodes bonded to the skin in order to take the electrocardiograms (ECGs). Bonded electrodes provide good electrocardiographic signal quality, but a period of installation on the patient is required, and they cause skin reactions and have to be periodically changed. Bonded electrodes are therefore not suitable for the above mentioned patients, such as infants, and for exposed personnel for example.

It has also been proposed to incorporate electrodes into an elastic garment worn by the patient, but the garment, although flexible and elastic per se, is restricted by the conducting cables that run through it, since these cables are not elastic (U.S. Pat. No. 6,080,690 and WO-A-01/02052). This results in a certain lack of comfort and often electrodes are incorrectly applied on the patient's skin.

In addition, the conducting cables and their connections constitute areas of increased thickness in the garment which may cause irritations, in particular on the delicate skin of newborns, and on adults if external loads are applied to the body at points where these conducting cables pass.

The electric power supply for the sensors also poses problems: the cells or batteries generally used have to be changed or recharged periodically, which requires maintenance operations over the course of long-duration medical monitoring, which operations are liable to interrupt this monitoring.

In devices currently available for monitoring infants, sensors are fixed to a garment or bonded to the baby's skin, and an electrical cable connects the garment worn by the baby to a nearby external module that delivers the power and receives the data from the sensors. This cable link constitutes an impediment and a hazard to the baby.

SUMMARY OF THE INVENTION

To solve these problems and to avoid the aforementioned drawbacks, the invention proposes a garment for the medical monitoring of a patient, comprising biomedical sensors, electrical power distribution and data transmission means and means for electrical power supply and for data transfer to means external to the garment, characterized in that at least some of the sensors, the electrical supply or distribution means and the data transmission or transfer means are formed from elastic conducting yarns integrated into and distributed over the fabric of the garment.

This garment has the advantage of imitating human skin and of reproducing, on that part of the body in question, a covering that has flexibility and elasticity properties, which contains flexible elastic integrated sensors and which conveys the signals emitted by the sensors onto electrical networks, the conductivity of which is controlled, that is to say a garment that behaves as a "second skin".

The garment can be used in a medical monitoring system that optimizes the compromises between the quality of the physiological signals received, the comfort and electrical autonomy, and this is applicable in particular to exposed personnel (professionals in a high-risk situation or top sportsmen for example), to newborns and young children, to clinical trials and to the elderly.

The electrical power is provided to the electronics of the garment via contactless external transfer. The monitoring system associated with the garment includes a means for collecting and locally processing the data from the sensors, the data being transferred contactlessly from the garment, and a remote server with which medical personnel may be connected in order to consult and interpret the data from the sensors received via a telecommunication or data transmission network.

Advantageously, the garment, or more generally a covering of part of the human body, worn close to the skin, has all the characteristics of mechanical protection, comfort, moisture removal and thermal insulation of a good flexible elastic undergarment that conforms to the body's shapes, while still including the integrated physiological sensors and flexible elastic conducting yarns, the physiological sensors (for example ECG electrodes or acoustic sensors) being pressed against the skin by the effects of their elasticity and that of the garment, without requiring adhesive bonding.

BRIEF DESCRIPTION OF THE SEVERAL VIEWS OF THE DRAWINGS

The invention will be more clearly understood on reading the description that follows, given by way of non-limiting example with reference to the appended drawings in which.

DETAILED DESCRIPTION OF THE INVENTION

Figure 1:
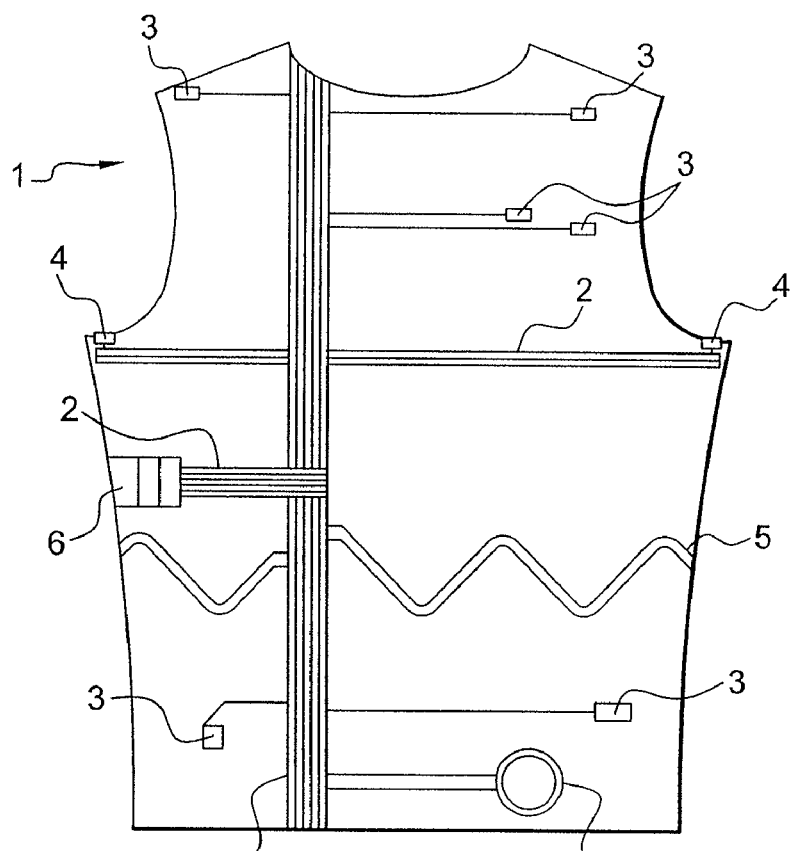
FIG. 1 is a schematic view of an undergarment into which conducting yarns and sensors are integrated.

FIG. 1 is a front view of an undergarment 1 (shown without sleeves) made of a fabric into which electrically insulated conducting yarns are integrated, some of the wires being grouped together in bands or ribbons 2 and 7. The garment 1 includes here a data transmission and power supply bus 7 of a type conventional in electronics (such as, for example, the I2C "fieldbus"), the bus being connected to a loop 8 which is an inductive coupling coil allowing power and/or data to be transmitted to a nearby coil (not shown and not forming part of the garment) which is not in direct contact with the garment.

The sensors integrated into the garment comprise, for example, ECG electrodes 3, temperature probes 4, means 5 for measuring change in the thoracic perimeter and an activity or position sensor 6.

The undergarment is made of a woven or knit consisting of non-conducting elastic yarns, for example of the type sold under the brand name ELASTANE by DuPont de Nemours, which ensure great flexibility and great elasticity, as in suits commonly used by sportsmen, all of the garment, or at the very least a major portion thereof, being formed from these non-conducting elastic yarns.

The conducting yarns, such as 2 and 7, integrated into the garment do not restrict the garment's elasticity or its comfort, since they are themselves elastic. A substantial advantage of the invention, which results from the great elasticity of the garment, is to limit the number of different sizes to be put on the market in order to comply with the various morphotypes of the users.

All the features described here as regards an undergarment apply to any flexible elastic covering of part of the body such as for example a neck muff, a sock, a sleeve, a glove, etc.

Figure 2:
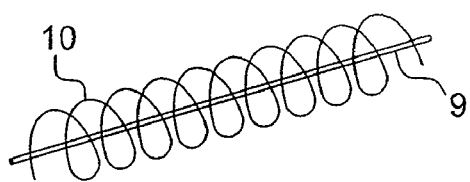
FIG. 2 is an enlarged view of a conducting yarn made elastic by winding around an elastic core (wrapping process)

FIG. 2 shows how, according to the invention, an initially non-extensible conducting yarn (a metal wire or a yarn made of a conductive polymer or a yarn made of a polymer filled or coated with a conductive material for example) is made elastic: the conducting yarn 10 is wound in a spiral around a core consisting of a non-conducting elastic yarn 9, which is made of a material such that, after it has been subjected to a tensile stress, it returns to its initial length, which is for example made of Elastane or of a similar material.

This winding operation, called wrapping, can be carried out by conventional machines in spinning workshops. The mechanical effect of the spiralled conducting yarn 10/elastic yarn 9 combination is two fold: when subjected to a tensile force, the assembly stretches in the direction of the tensile force, opposing a reaction like a spring (the elastic core 9 and the spiral 10 resist together in the same direction); and, when the tensile force is removed, the assembly is returned to its initial length by the elastic core 9, which compresses the conducting spiral 10. It is possible to wind another textile yarn around this assembly. This operation, called reverse wrapping, does not impair the elasticity of the resulting assembly and has the purpose of improving its strength and its weaveability.

Using an elastic core 9 having mechanical properties and a diameter that are similar to those of the other elastic yarns used in the fabric of the garment, and a fine flexible conducting yarn 10 with a diameter of a few tens of microns (typically 20 to 40 μm) which may or may not have an electrically insulating coating, depending on the use of the yarn, the elastic conducting yarn obtained by wrapping behaves, during weaving or knitting, like the other elastic yarns. The resulting fabric, in which the elastic conducting yarns are woven or knitted, behaves in a homogeneous manner, without any hard or non-elastic points or areas. The fabric is cleanable and washable with the same ease and constraints as if it were to contain no conducting yarns. The garment made up with this fabric has all the flexibility and elasticity properties of a garment having no integrated conducting yarns.

Depending on the usage of the conducting yarn in the garment, the yarn is bare (contact with its surface is therefore conducting) or provided with an electrically insulating coating.

For example, the conducting electrodes applied against the skin are made with bare yarns. Such electrodes may serve to collect electrical signals generated by the body (for the construction of an electrocardiogram or an electromyogram for example), or to transmit power or pulses to the body. Likewise, a mechanical deformation sensor is produced with bare yarns, the electrical contact between the adjacent elastic turns 10a and 10b of which (FIG. 3) vary with the elongation that is imposed thereon, resulting in a measurable change in electrical resistance that depends on the elongation. Such an elastic sensor integrated into the garment is useful for measuring, for example, changes in the patient's thoracic perimeter or the deformations of the muscles and joints.

The electrically insulated conducting yarns are used, for example, to transmit signals and electrical power in the garment.

The elastic conducting yarns integrated into the fabric must be able to be electrically connected to one another and to electronic components (for example sensors and connectors) integrated into the garment.

It is known that good fixed electrical connections are made by soldering two conductors together, but also that the conductors break near the soldered joints when they are flexible and subjected to mechanical loads. Now, in the garment according to the invention, the conducting yarns are subjected to frequent mechanical loads because of their elasticity. The invention avoids these problems due to soldering between conductors using only the mechanical properties of the spirally wound elastic conducting yarns in order to electrically connect them.

Figure 3:
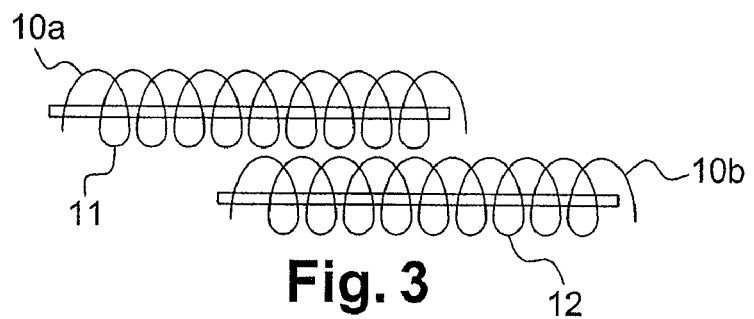
FIGS. 3 and 4 show conducting links between two elastic conducting yarns.
Figure 4:
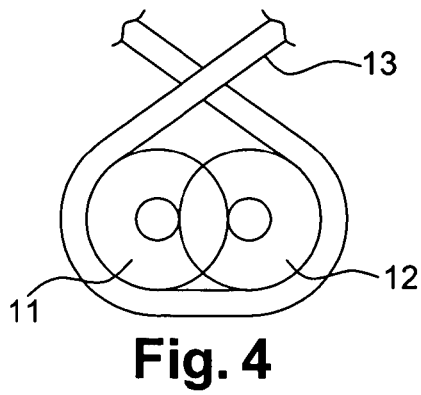

FIGS. 3 and 4 illustrate a method according to the invention of electrical connection between two elastic conducting yarns 11 and 12. Firstly, if the yarns are electrically insulated, the electrical insulation that covers each conducting yarn 10a and 10b of the composite yarns 11 and 12 is removed over a short length of each composite yarn. To do this, various methods can be applied, for example the chemical action of a substance that dissolves or destroys this insulation, or the abrasive mechanical action of a jet of air containing abrasive particles, or heating using a point heat source (for example a laser beam focused on to the area to be stripped). The stripped portions of the two composite yarns are then brought together (FIG. 3) and held firmly and definitively in place, one against the other, by tight binding stitches produced by means of a thread 13 (FIG. 4), which may itself be conducting, using a sewing machine. FIG. 4 shows the binding before the thread 13 is tightened, for greater clarity since, after tightening, the various yarns are squashed against one another.

Figure 5:
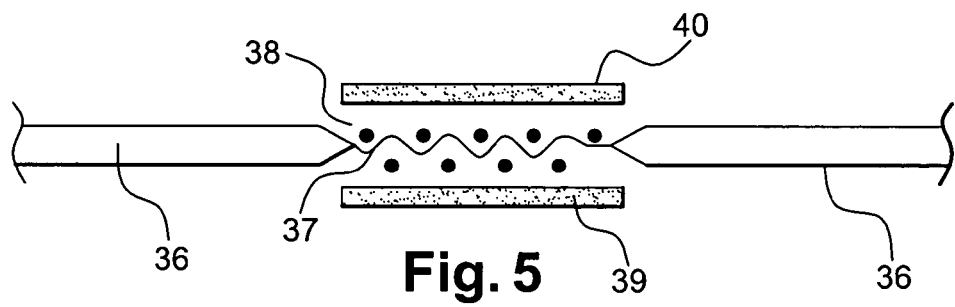
FIG. 5 shows an alternative embodiment of the link.

In a variant illustrated in FIG. 5, the binding between two yarns or two ribbons of conducting yarns 37 and 38 (for example, the yarns 37 are weft yarns and the yarns 38 are warp yarns in the fabric 36) is provided by strongly applying, and possibly by heating, a small pad 39, 40 on each side of the connection to be produced. The two pads, at least one of which is electrically conducting, are held firmly in place, one against the other, clamping and squashing the yarns 37 and 38 to be connected together, for example when the said pads are made of conductive adhesive materials or they contain the solder for electrical connection, which has been heated and has impregnated the conducting yarns, or are stitched together. This mode of connection is also suitable for electrically linking yarns in a knit or else for connecting yarns foreign to the fabric to those of the fabric. In this case, the pads clamp the yarns of the fabric and the foreign yarns at the same time.

These pads may be made of a conducting metal, for example copper, or a flexible material such as kapton with solder or the like deposited thereon. It is also possible to use, not solid pads, but small meshes, the yarns of which include solder or the like.

Finally, an electrically insulating material (for example a flexible insulating varnish or flexible adhesive tape) is deposited on the connection thus produced, in order to restore, if necessary, the electrical insulation. Thus, a connection without any hard mechanical point is obtained, the mechanical properties of which, in particular the elasticity, are homogenous with those of the other yarns (whether conducting or non-conducting) of the fabric.

Figure 6:
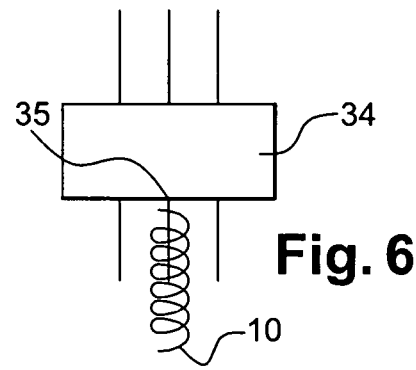
FIG. 6 shows a conducting link between an elastic conducting yarn and a non-elastic component.

FIG. 6 shows how an electrical connection between an elastic conducting yarn 10 and a non-elastic electronic component 34 may be made using again the mechanical properties of the spiral of the conducting yarn; this spiral is forced to cover the pin 35 of the component to be connected, over a sufficient length to ensure good electrical contact, then the contact is reinforced, for example using a conductive adhesive, and finally an insulating layer is deposited on the connection. A kind of mechanical crimping is thus carried out. The non-elastic component may itself be flexible if it is produced, for example, on a thin support that can deform by bending or twisting, such as a Kapton film sold by DuPont de Nemours.

In order for the conducting yarns in the middle of the non-conducting yarns to be easily identified and for the locally stripped areas to be checked, luminous marking may be carried out according to the invention by incorporating pigments into the insulating outer layer of the conducting yarns, these pigments not being visible in natural light but visible under certain special types of illumination, for example in ultraviolet light.

The connection methods described above can be easily automated and allow the conducting yarns to be electrically connected in the fabric, before or after the garment is made up. For example, it is in this way that the conducting yarns of the ribbons 2 (FIG. 1) that go to the sensors 3, 4, 5 and 6 are connected to the conducting yarns of the ribbon 7 in order to form the electronic bus for the garment.

Figure 7:
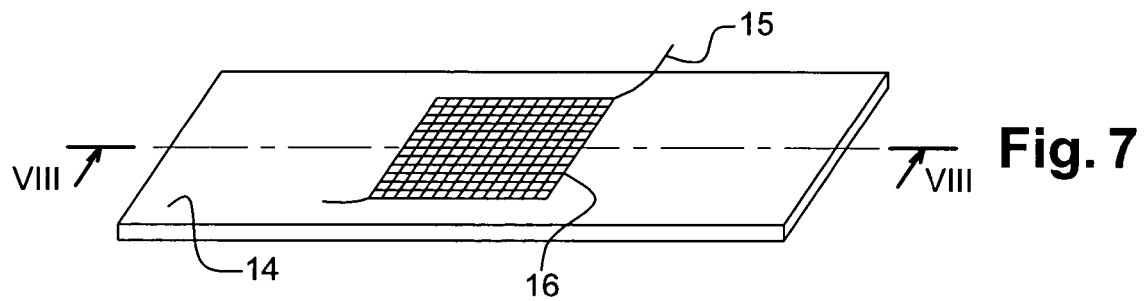
FIGS. 7 and 8 show an example of a flexible sensor woven into the fabric of the garment.
Figure 8:
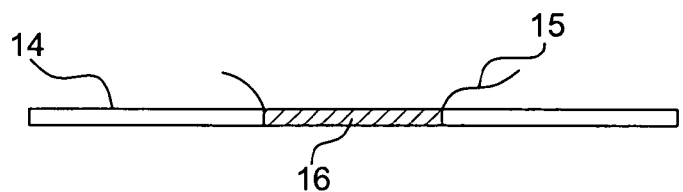

FIGS. 7 and 8 show how the flexible sensors are integrated into the fabric of the garment. The example illustrated is an ECG electrode, formed by crocheting a fine, flexible, non-insulated conducting yarn 15 into the fabric 14 in order to form a piece 16 measuring about $2 \times 2$ cm$^2$ in area. The incorporation of this piece 16 can be achieved on Jacquard-type looms using what is called the "brocade batten" technique. The yarn with which the electrode 16 is made may, for example, be made of stainless steel, silver- or gold-plated copper, or made of solid gold or of conductive polymers. The connection between such a sensor and the elastic conducting yarns of the bus 7 is achieved by the method explained above whereby stripped portions are brought together, and then clamped together by binding threads.

In a variant of the invention, the electrodes or the conducting parts of the garment are not integrated into the fabric, but are the fabric itself. For example, the fabric is completely produced from conducting yarns made of an insulating polymer coated with a conducting metal. Those areas where conduction of the yarns is not desired (for example around an electrode) are chemically or electrochemically treated (for example by electrolysis) in order to remove the metal coating from the polymer yarns, thereby making the area non-conducting away from the conducting part that has been preserved. Conversely, a non-conducting area of the fabric may be made conductive using the same chemical or electrochemical methods or by impregnating the area to be treated with a conductive material or by spraying a conductive material on to the area to be treated. These methods allow the conductivity of the fabric to be varied at will, even after weaving, thereby providing great flexibility in the designing of the garment and in adapting it to its operating conditions.

Figure 9:
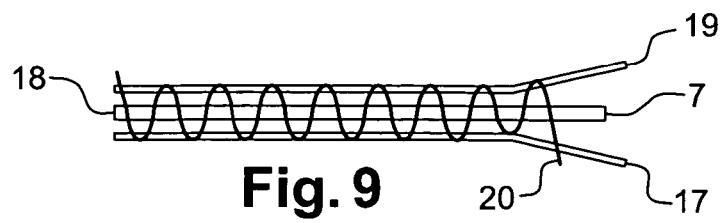
FIG. 9 is a schematic sectional view of a fabric produced as several woven or knitted layers.

FIG. 9 is a sectional view of a fabric for the garment according to the invention, formed from several layers joined together, for the purpose in particular of providing the garment with electromagnetic protection.

When the garment is used with integrated conducting yarns and sensors, the conducting yarns distributed within the garment may act as antennas with respect to undesirable electromagnetic phenomena, received from the outside and radiated from the inside. The standard remedy against such interference is to screen the yarns by conducting layers that surround the yarns that it is desired to protect. According to the invention, the method of electromagnetically screening the garment consists in inserting the layer 18 (FIG. 9) in which the conducting ribbons to be protected, such as, for example 2 and 7 (FIG. 1), between a ribbon of insulated conducting yarns woven in a layer of fabric 17 underneath and another ribbon of insulated conducting yarns woven in a layer 19 on top. The conducting ribbons of the layers 17 and 19 are electrically connected together at certain points in the garment and are connected to an electrical potential level generally called "earth". In addition, each layer may play a precise differentiated role in the comfort of the garment, as is known in the case of multilayer fabrics.

The various layers that form the complete fabric are fastened together by means of yarns 20 using a standard weaving or sewing method.

Figure 10:
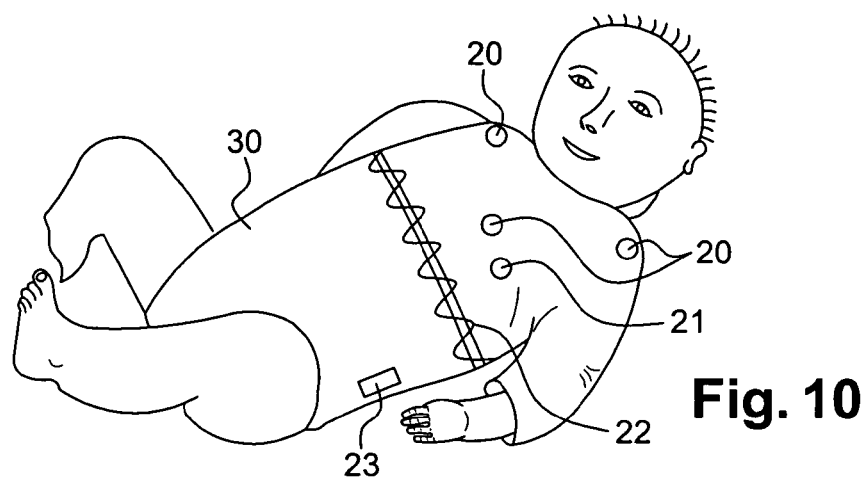
FIG. 10 shows a newborn wearing a garment according to the invention.

FIG. 10 shows an infant wearing a garment 30 according to the invention, more particularly one suitable for monitoring infant apnoea. To simplify the drawing, the conducting yarns have not been depicted, only the sensors integrated into the garment having been shown. The parameters for monitoring infant apnoea, for the purpose of preventing possible sudden death of the infant, are preferably the following: heart rate, obtained for example using flexible textile electrodes 20 applied against the skin, or using a ballistometer (an electroacoustic sensor) 21 placed close to the heart, and the breathing rate, obtained, for example by recording the breathing movements using a plethysmograph 22 placed around the base of the infant's thoracic cage. It has been found that the number of sudden infant deaths decreases if babies are made to sleep on their back. After they are a few months old, babies laid on their back to sleep have a tendency to try to turn back over and therefore unconsciously return to a more dangerous position. It is important for those around the baby to be informed of any change in position of the baby on his bed. Advantageously, the position sensor 23 integrated into the garment detects whether or not the infant is on his back; the signals from this sensor are transmitted and analysed like those from the other sensors.

In order not to restrict the comfort and ease of use of the garment, it is necessary to limit the number of electronic cards and power supplies to be fitted on to the garment. To do this, the invention proposes to transmit electrical power and data between the garment and its close physical environment by methods that do not require any physical contact with the garment. In the present invention, a circuit called the secondary circuit is in the garment, and this receives the energy from another circuit, called the primary circuit, which is connected to an electrical power supply external to the garment, a low-voltage (for example 6 to 24 volts) AC current flowing through this primary circuit.

Each circuit comprises a multiturn coil. The coil of the primary circuit creates an induction field that is picked up by the coil of the secondary circuit placed nearby and thus sufficient power to operate the sensors is transferred from the external power supply to the circuit in the garment. The efficiency of this inductive coupling method can be increased by placing ferromagnetic cores in the middle of the coils. The coil of the secondary circuit in the garment can be produced from the elastic conducting yarns according to the invention in order not to limit the flexibility and elasticity of the garment at this point, for example using a Jacquard loom with brocade battens. The ferromagnetic core of the flexible secondary coil may itself be flexible by using, for example, supports made of flexible synthetic foam filled with ferromagnetic particles.

Figure 11:
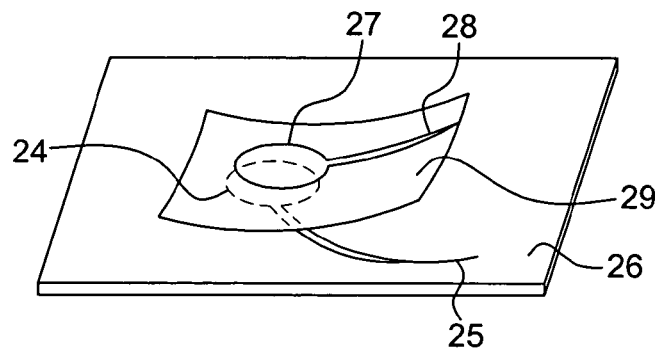
FIG. 11 is a partial view showing the position of the coupling coils for contactless transfer between the circuits in the garment worn by a baby and the cover of the mattress on which he is sleeping.

FIG. 11 shows an example of inductive coupling between a coil 24 (shown in dotted lines) of the primary circuit 25 integrated into the sheet 26 or the mattress cover of the baby's bed and a coil 27 of the secondary circuit 28 integrated into the back of the baby's garment 29 (only a small area of which has been shown) which remains close to the primary coil 24, since the baby has been laid on his back against the sheet.

Should there be a malfunction of the inductive coupling, for example due to excessive separation between the coils 24 and 27, and to guarantee operation of the system, the power needed to operate the garment may be supplied by emergency batteries or cells, or else by "supercapacitors" (i.e. capacitors of large capacitance in a small volume) while waiting, for example, for the coils to be once again brought back close together by an external assistant alerted by the warning means. The cells may be mounted in the garment at a point causing little bother, such as the rear of the baby's garment, level with the soft thickness formed by his disposable nappy.

The inductive coupling method applies to garments for adults, the primary and secondary coils being kept close together, for example, in a trouser or skirt belt, or at any other point where the relative movements of the primary coil with respect to the secondary coil in the garment are limited.

Contactless transfer of the data delivered by the sensors in the garment to a receiving base nearby may also be carried out by inductive coupling. Alternative forms of the transfer methods use wireless data exchange means available in the industry, for example, by short-range radio (of the Bluetooth or other type), by infrared or else by ultrasound.

The remote medical monitoring system associated with the garment comprises modules, external to the garment, especially a module for supplying power to the garment by inductive coupling, a module that receives the data from the sensors in the garment, a local data processing module, a module for alerting those around the patient, in order to give him assistance, and a module for transmitting data to a remote station (a server). Some or all of these modules may be grouped together into a single module called a "close receiver base", located close to the garment in use. In applications of the invention for adults, the close receiver base may be installed, for example, in a pouch or pocket of the person wearing the garment. In applications for newborns and young infants, the receiver base may be placed on the infant's bed or beside it.

The module for alerting those around the baby may advantageously be connected to a commercial transmitter, which allows his parents to hear, from a distance, by short-range radio, the sounds uttered by the baby in a neighbouring room.

The module for transmitting data to a remote station generally comprises a modem connected to a data exchange network, such as the telephone network, or a radio communication network (for example, a GSM network) or a specific radio communication means for exposed personnel (military personnel, firefighters, sportsmen, etc.).

When the person wearing the garment is moving about, the medical monitoring system may advantageously be supplemented with a means of locating the person wearing the garment, such as the GPS (Global Positioning System) or system for global location of GSM mobile telephony network operators. The location is transmitted to the remote station in the same way as the data coming from the garment.

Figure 12:
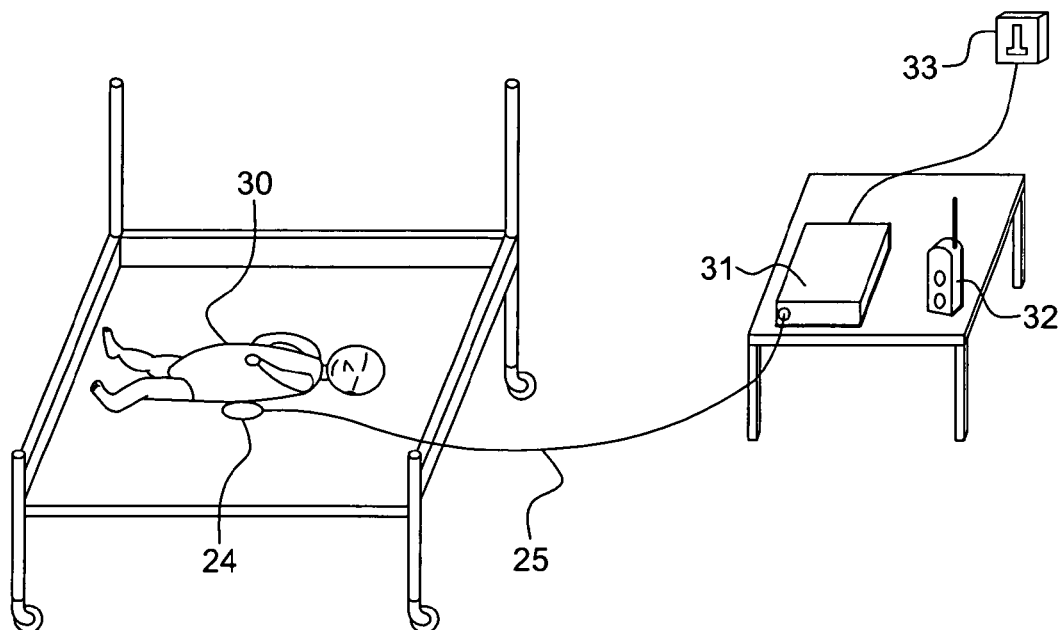
FIG. 12 shows an installation for monitoring the sleep of the infant.

FIG. 12 shows an example of a complete installation of a system for monitoring an infant in his bed. The baby is wearing a garment 30 according to the invention, such as, for example the one shown in FIG. 9. The inductive coupling coil 24 of the primary power circuit 25 is the only one shown, for the sake of clarity of the drawing. The coil 24 is integrated into the mattress cover, from which extends the cable 25 of the primary circuit, connected to the close receiver base 31 placed beside the bed. Data from the sensors in the garment is transferred to the receiver base 31, again by inductive coupling, but the corresponding circuits are not depicted. The base 31 contains batteries that supply the primary power. The local processing means and the warning means are contained in the receiver base; the warning means is connected to a short-range radio device 32 operating on cells or batteries of the type of those allowing the parents to listen out for the sounds made by the infant in a neighbouring room. This radio device constitutes, in this example, the means for warning those around the baby. The close base 31 also contains a modem for transmitting the data from the sensors to a remote server, in this example via the wire telephone network, represented here by a telephone socket 33. Such a system installation provides the infant with double electrical insulation with respect to the housing's electrical system. The data, teletransmitted to the server, is examined and interpreted by the treating doctor and an expert in a manner known per se (FR-A-2 717 332 and FR-A-2 760 962).

The invention claimed is:

1. Garment for the medical monitoring of a patient, comprising biomedical sensors, an electrical power distribution and data transmission bus connected to the sensors and to a coupling circuit for allowing electrical power supply and data transfer to a circuit external to the garment, wherein at least some of the sensors, the electrical power distribution and data transmission bus and the coupling circuit are formed from elastic conducting yarns integrated into and distributed over the fabric of the garment, wherein the elastic conducting yarns consist of fine conducting yarns wound in a spiral around a non-conducting elastic core.

2. Garment according to claim 1, wherein sensors formed from elastic conducting yarns are integrated into the fabric of the garment while the garment is being woven.

3. Garment according to claim 1, wherein a conducting connection between two elastic conducting yarns is produced by contact between the spirals of the two elastic conducting yarns, the contact being maintained by binding stitches that clamp the two conducting yarns against each other.

4. Garment according to claim 1, wherein a conducting connection between two conducting yarns is produced by clamping the yarns, pressed against each other, between two pads or meshes fastened together, at least one of which is conducting.

5. Garment according to claim 1, wherein at least one of the sensors measures mechanical deformations of that part of the body on which it is applied, by recording electrical effects due to the mutual sliding of the spirals of the fine conducting yarns when the fabric is pulled in the direction of the conducting yarns.

6. Garment according to claim 1, wherein the conductivity of the conducting yarns is modified by chemical or electrochemical treatment or by impregnation with a conductive or insulating material to create conducting areas and non-conducting areas.

7. Garment according to claim 1, wherein the garment consists of several superposed fabric layers that contain conducting yarns for protecting components of the garment from undesirable electromagnetic effects, the said layers being held in place against one another by yarns that pass through them.

8. Garment according to claim 1, wherein the electrical power distribution and data transmission bus comprises a bus of insulated elastic conducting yarns, to which the sensors are connected.

9. Garment according to claim 1, wherein the coupling circuit for electrical power supply comprises a contactless inductive coupling circuit integrated into the garment.

10. Garment according to claim 1, wherein the coupling circuit for electrical power supply and for data transfer includes a contactless link for transferring data picked up by the sensors in the garment to a close receiver base associated with said circuit external to the garment.

11. Garment according to claim 1, additionally including a module for transmitting data delivered by the sensors, via a telecommunications network, to a server that is used by medical personnel.

* * * * *